United States Patent [19]
Heirtzler et al.

[11] Patent Number: 5,426,972
[45] Date of Patent: Jun. 27, 1995

[54] MONITORING SOIL COMPACTION

[75] Inventors: Frank J. Heirtzler, Londonderry, N.H.; Robert L. Cardenas, Framingham, Mass.; David M. George, Marlboro, Mass.; Kenneth A. Pasch, Chicago, Ill.; Daniel R. Deguire, Blackstone, Mass.

[73] Assignee: Gas Research Institute, Chicago, Ill.

[21] Appl. No.: 49,076

[22] Filed: Apr. 20, 1993

[51] Int. Cl.[6] .................. G01N 33/24; G01N 29/18; G01V 1/50
[52] U.S. Cl. ...................... 73/84; 73/12.01; 73/784; 73/594; 73/597; 405/271
[58] Field of Search .............. 73/12.01, 78, 84, 594, 73/597, 784; 405/271

[56] References Cited

U.S. PATENT DOCUMENTS

| Re. 31,195 | 4/1983 | Thurner . | |
|---|---|---|---|
| 3,456,596 | 7/1969 | Heller . | |
| 3,641,181 | 2/1972 | Gnaedinger, Jr. et al. . | |
| 3,998,090 | 12/1976 | Wislocki . | |
| 4,149,253 | 4/1979 | Paar et al. | 364/505 |
| 4,348,901 | 9/1982 | Vural et al. . | |
| 4,467,652 | 8/1984 | Thurner AB et al. | 73/594 |
| 4,495,434 | 1/1985 | Diepers et al. . | |
| 5,105,650 | 4/1992 | Atkinson et al. . | |
| 5,177,415 | 1/1993 | Quibel et al. | 73/573 |

FOREIGN PATENT DOCUMENTS

| 134557 | 6/1987 | Japan | 73/597 |
|---|---|---|---|
| 973702 | 11/1982 | U.S.S.R. . | |
| 1318653 | 6/1987 | U.S.S.R. . | |
| 9114182 | 9/1991 | WIPO | 73/594 |

OTHER PUBLICATIONS

Database WPI, Week 8842, Derwent Publications Ltd., London, GB; AN 88-299228 & SU-A-1 388 799 (Ind Build Res Inst) 15 Apr. 1988 (abstract).
Database WPI, Week 8926, Derwent Publications Ltd., London, GB; AN 89-191447 & Su-A-1 449 864 (Urals Rail Transp Inst) Jan. 1989 (abstract).
De Alba, *Use of Bender Elements in Soil Dynamics Experiments, Recent Advance in Instrumentation, Data Acquisition and Testing in Soil Dynamics*, American Society Civil Engineering, Oct. 21, 1991, pp. 86-101.
Agarwall, *Multi-Directional Wave Velocity by Piezoelectric Crystals, Recent Advance in Instrumentation, Data Acquisition and Testing in Soil Dynamics*, Am. Society Civil Engineering, Oct. 21, 1991, pp. 102-117.
Gohl, *Use of Piezoceramic Bender Elements in Soil Dynamics Testing, Recent Advance in Instrumentation, Data Acquisition and Testing in Soil Dynamics*, Am. Society Civil Engineering, Oct. 21, 1991, pp. 118-136.

*Primary Examiner*—Hezron E. Williams
*Assistant Examiner*—Daniel S. Larkin
*Attorney, Agent, or Firm*—Fish & Richardson

[57] ABSTRACT

Methods and apparatus for determining whether soil is satisfactorily compacted. An operator delivers impact energy to the soil, and the amount of impact energy transmitted through the soil is repeatedly sensed and stored. A modelling formula, which approximates the variation of the stored amounts of impact energy, is used to generate current and target values for the level of compaction; if the current value equals or exceeds the target value, the soil is considered to be satisfactorily compacted.

14 Claims, 6 Drawing Sheets

FIG. 3
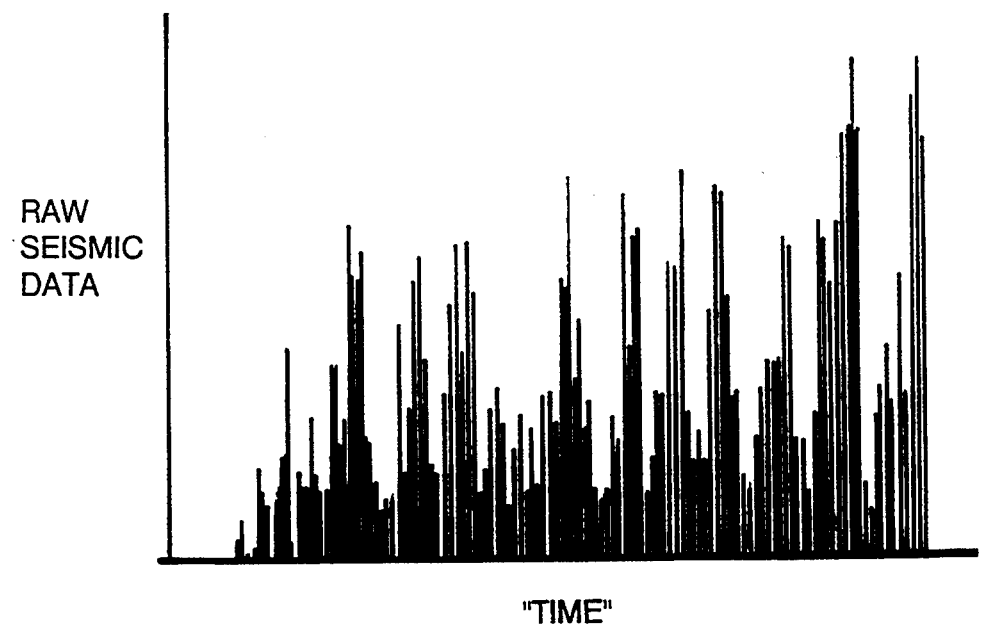
RAW SEISMIC DATA
"TIME"
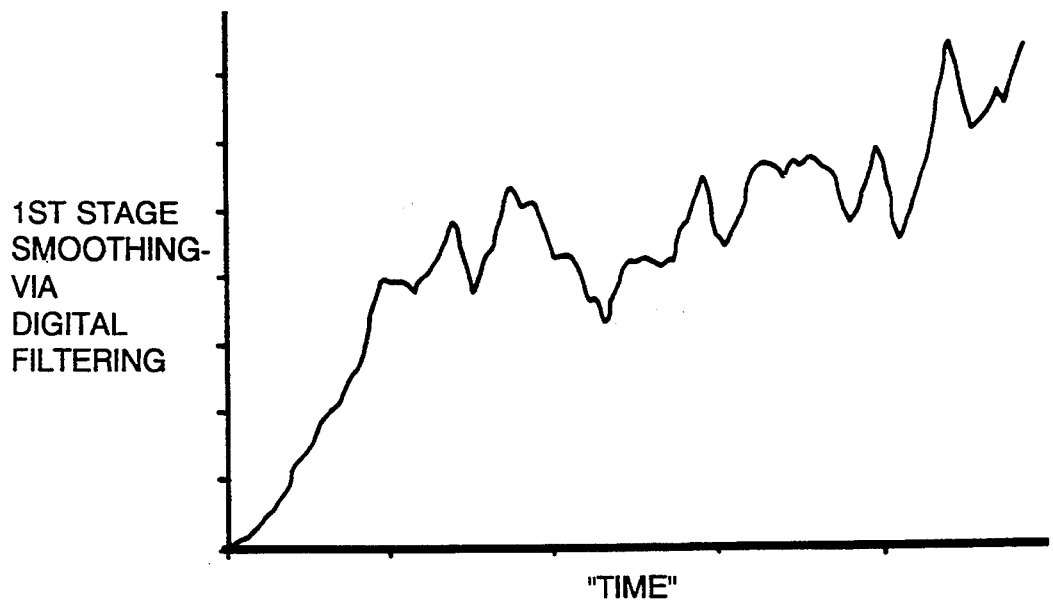
1ST STAGE SMOOTHING- VIA DIGITAL FILTERING
"TIME"
FIG. 4

MONITORING SOIL COMPACTION

BACKGROUND OF THE INVENTION

This invention relates to monitoring systems which detect the compaction of soil in backfilled excavations.

Excavations such as utility trenches, foundations and the like are generally backfilled in layers known as lifts. Each lift of backfill material is compacted before the addition of the next lift. If the backfill material is improperly compacted, or if an unsuitable backfill material is used, the backfilled excavation may subside. Subsidence under a foundation, roadway or other structure can lead to costly repairs.

U.S. Pat. No. 5,105,650 to Atkinson et al., which is assigned to the assignee of this application and is incorporated by reference herein, discloses an apparatus for monitoring the compaction of soil which includes a hammer for delivering impact energy to soil material and a piezoelectric sensor at the bottom of the backfilled region for monitoring the amount of impact energy delivered to the backfill. The sensor transmits electrical signals representing the received impact energy to a control module which analyzes these signals to determine when satisfactory compaction is achieved.

SUMMARY OF THE INVENTION

Compacted material transmits more impact energy than uncompacted material. As a result, the peak amplitude of the sensor signals increases gradually toward a maximum as the backfill is compacted; this increase in peak amplitude can be used to measure the progress of compaction, and a termination of increases can be used to indicate that satisfactory compaction has been achieved. It has been found, however, that compaction is not necessarily satisfactorily complete even though the peak amplitude has reached what might appear to be a maximum value. It is therefore an object of this invention to measure the progress of material compaction by monitoring the peak amplitude of impact energy collected by a sensor, in a manner which does not rely solely upon increases in the average peak amplitude as an indicia of compaction.

The invention provides a method for determining whether compactable material is satisfactorily compacted. As impact energy is delivered to the compactable material, data on the amount of impact energy transmitted through the material are repeatedly sensed and stored. Then, signals representative of the current level of compaction of the material and a target level of compaction are generated from the stored progression of impact energy data; if the current value equals or exceeds the target value, the material is considered to be satisfactorily compacted.

In a particular embodiment, the material is soil and the estimates of current and target levels of compaction are generated by a modelling formula which approximates the progression of stored impact energy data. This modelling formula may be of the type which approaches a fixed asymptotic value, in which case the target value can be derived from a fraction of the asymptotic value. One suitable formula is $$10^{\frac{t}{b+mt}}$$

where t is the number of the current impact energy data point, and b and m are parameters which are adjusted to approximate the formula to the progression of data.

Impact energy may be measured by storing the peak amplitude of an electrical signal. Peak amplitudes smaller than a predetermined threshold may be ignored. Also, the measured peak amplitudes may be low-pass filtered, for example by averaging them. The filtered peak amplitudes may then be subjected to a logarithmic transformation, and the transformed amplitudes subjected to a linear regression using a weighting formula.

Other features and advantages of the invention will be seen as the following description of a particular embodiment progresses, in conjunction with the drawings, in which:

BRIEF DESCRIPTION OF THE DRAWING

FIG. 3 is a graph of the impact energy signals received by the sensor 30 as one of the lifts 14–18 is being compacted;

FIG. 4 is a graph of the impact energy signals of FIG. 3 after smoothing via a digital low-pass filter;

DESCRIPTION OF PARTICULAR EMBODIMENT

Figure 1:
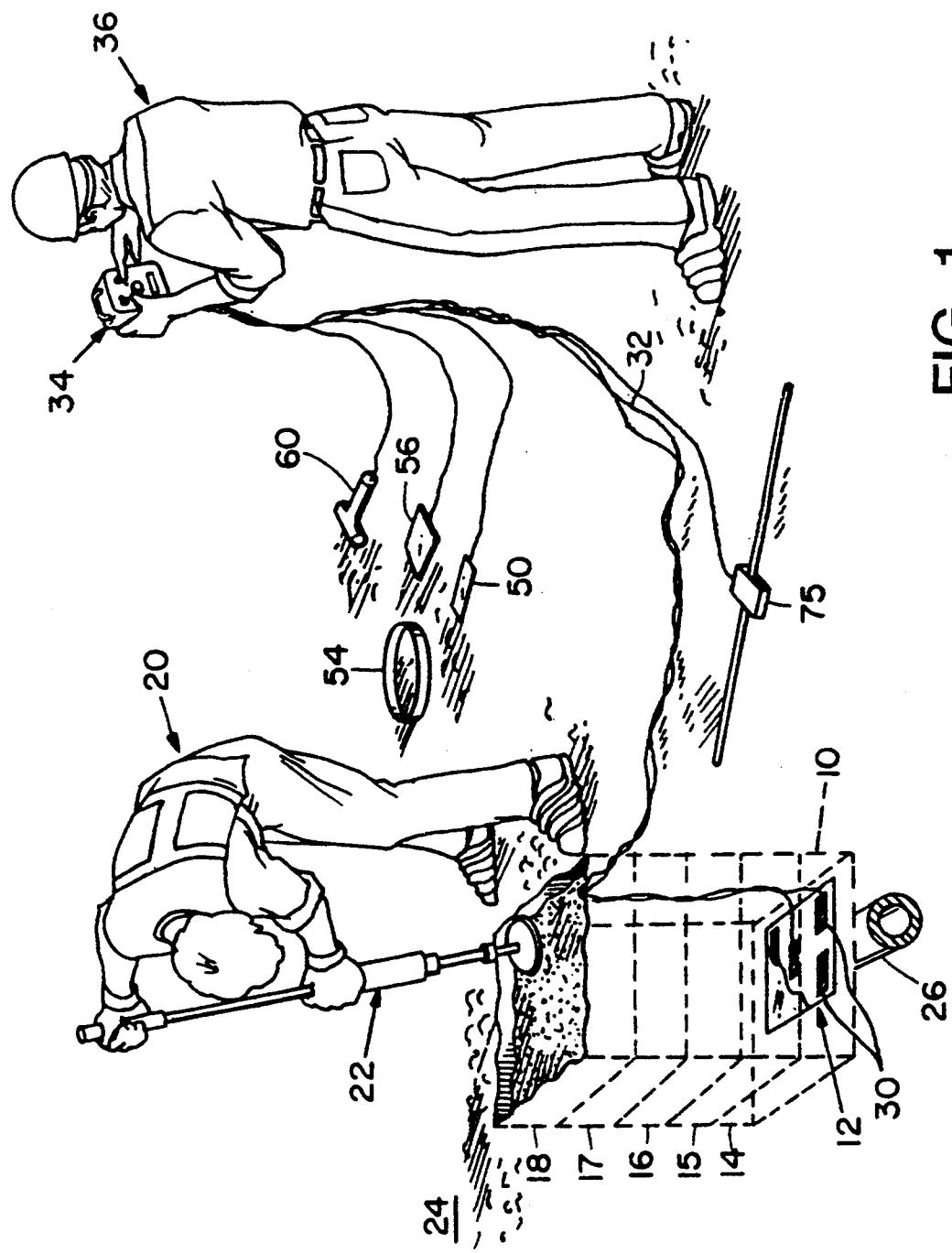
FIG. 1 is a diagrammatic view of a compaction monitoring system.

A soil compaction monitoring system is shown diagrammatically in FIG. 1. Excavation 10 in road surface 24 (for repair of gas line 26) is being backfilled by a series of five lifts 14–18. Operator 20 is using impact tool 22 to compact the uppermost lift 18. Sensor module 12, which includes an array of piezoelectric transducer strips 30, is disposed underneath the lowermost lift, and is connected to battery-powered portable control module 34 via conductors 32. Observer 36 is operating control module 34.

As shown, to backfill an excavation using the above system, sensor module 12 is placed at the bottom of the excavation 10 with connecting conductors 32 leading up out of the excavation to the control module 34. After each lift of backfill material is placed in the excavation, the lift is compacted with compaction tool 22 (which may be manual, pneumatic or hydraulic). Each compacting blow from compacting tool 22 transmits seismic energy through the backfill lift(s) to the sensors 30 which produce output voltages corresponding to the sensed impact energies. These voltages are measured and stored by control module 34.

Further details of sensor module 12, and a description of PVDF proofing sensor 50, cylindrical spacer 54, metal trigger plate 56, proofing hammer 60 and transmitter-receiver unit 75, can be found in above-referenced U.S. Pat. No. 5,105,650.

Figure 2:
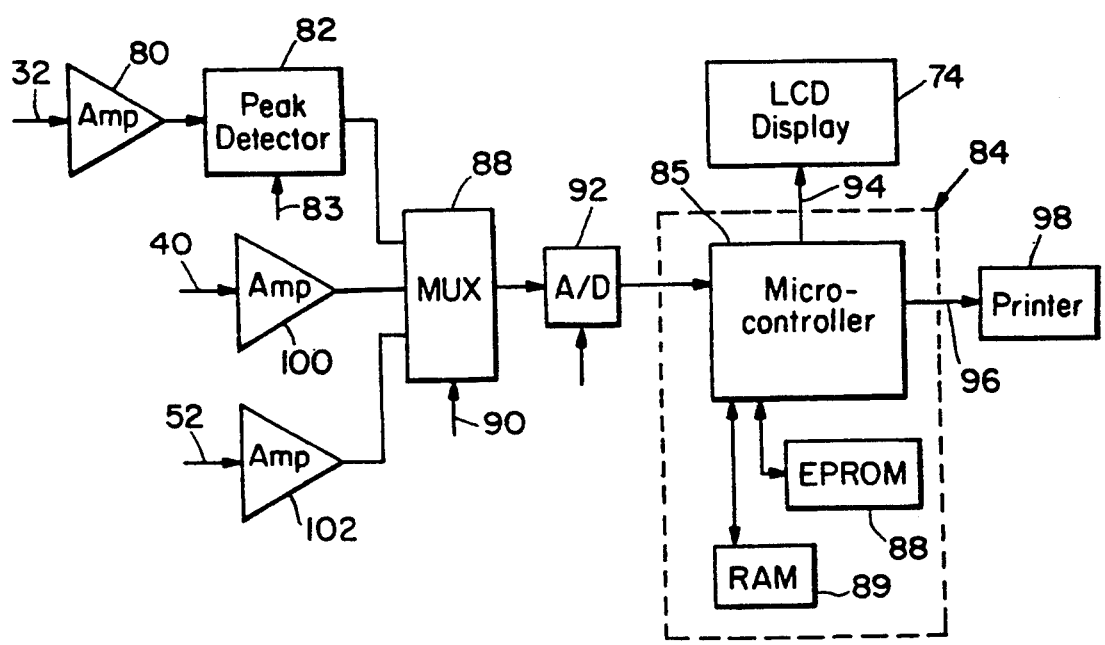
FIG. 2 is a block diagram of the circuitry of the control module 34 of FIG. 1.

Referring to FIG. 2, input lines 32 (from sensors 30 that are connected in parallel) are connected through adjustable gain amplifier 80 to peak detector 82. The peak detector 82 is enabled by microprocessor 84 via an input 83. The output of peak detector 82 is applied, via a multiplexer 88, to an analog to digital converter 92. Other analog inputs on lines 40 and 52 may also be routed to analog to digital converter 92 via multiplexer 88, as determined by a selection signal on control input 90. Microcontroller 85, in response to programming on EPROM 87, reads input from multiplexer 88, stores and retrieves data in RAM 89, and generates output on LCD display 74 or printer 98.

In operation, peak detector 82 tracks the analog signal on lines 32 and outputs the peak value of this analog signal. The peak value produced by peak detector 82 is converted by analog to digital converter 92 to an equivalent digital value, which is read and stored by microcontroller 85 in accordance with the program in EPROM 87. After microcontroller 85 has read a value from analog to digital converter 92, microcontroller 85 resets peak detector 82 (via line 83); peak detector 82 then cancels the currently stored peak value and begins tracking the input on line 32 to detect a new peak value.

In this way, during the periods between reset signals, peak detector 82 "memorizes" the maximum amplitude of the signal on lines 32. Thus, by periodically reading the output of peak detector 82 and then resetting peak detector 82, microcontroller 85 can separately measure the peak amplitude of the seismic signals received by sensor 20 during each time period. (In the following, the operation of reading and resetting peak detector 82 will be referred to as "sampling the peak detector", a peak value read from peak detector 82 will be referred to as a "sample" and the time period between each reset signal will be referred to as the "sampling interval".)

It is advantageous to separately measure the seismic signals from each individual compacting blow; for this reason, in one embodiment microcontroller 85 samples the peak detector at a high frequency, e.g. ten times a second, to ensure that, even if a hydraulic compacting tool is used to generate compacting blows, the seismic signals generated by each compacting blow will be individually sampled. Note, however, that the frequency of the compacting blows may be slower than the sampling frequency, and furthermore operator 20 may occasionally tire and temporarily stop issuing compacting blows altogether. As a result, many samples obtained by microcontroller 85 will have a near-zero value (because no compaction blows were landed during the sampling interval for the sample); these near-zero samples contain no useful information about the compaction of the soil and can be discarded, as described below°

Over time, as compacting blows are imparted to a lift, the samples from peak detector 82, which initially are at a low level, gradually increase toward a maximum value. Thus, as illustrated in FIG. 3, a graph of sample magnitude versus impact demonstrates a monotonically increasing average magnitude. However, as also illustrated in FIG. 3, this increase in average value is difficult to perceive because the sample magnitudes have high-frequency variations due to various factors such as the movement of the source of the compaction blows over the surface of the lift, variation in soil quality from one area to another, and random seismic disturbances caused, for example, by passing vehicles.

The elapse of time per se bears little relation to the compaction of the lift; the most important factor in the compaction of the lift is the number of compacting blows delivered by operator 20. Furthermore, it should be understood that the apparatus shown in FIG. 2 does not in fact track the elapse of time, rather, this apparatus only tracks the number of compacting blows delivered to the lift: as mentioned above, microcontroller 85 discards near-zero samples from peak detector 82, so that if, for example, operator 20 tires and temporarily stops delivering compacting blows, microcontroller 85 will cease storing samples even though time is elapsing. Furthermore, by discarding near-zero values, microcontroller effectively ignores compaction blows delivered at portions of the excavation which are distant from sensor 20. Thus, the horizontal axes in FIGS. 3-7 are labelled "IMPACT" the horizontal axes in those figures in fact, or the number of compacting blows delivered nearby; furthermore, although compaction may be described in the following text as a function of time, compaction is in fact primarily a function of the number of blows delivered, rather than time.

The high-frequency variations illustrated in FIG. 3 can be reduced by digitally filtering the samples retrieved from peak detector 82. FIG. 4 illustrates a low-pass filtered version of the samples of FIG. 3. The digital filter used to generate the data of FIG. 4 utilizes a "window average", that is, each filtered sample of FIG. 4 is equal to the average of n unfiltered samples from FIG. 3. (In one embodiment, the n most recently preceding samples are averaged, so that the first sample on FIG. 4 is generated from the average of the first sample on FIG. 3 with $n-1$ zeros, and the last sample on FIG. 4 is generated from the average of the last n samples on FIG. 3. In other embodiments other collections of nearby samples may be averaged or otherwise filtered.) The value of n is chosen to achieve the appropriate amount of high-frequency rejection. It has been found that, for a round, 12 inch diameter and 8 inch deep excavation, an effective low pass filter computes each filtered sample by averaging a window of 5 seconds of unfiltered samples (thus if the samples are collected 10 times per second, n would be 50). For a larger excavation 5 feet square and 4 feet deep, a 30 second window is needed (i.e., for 10 samples per second, n would be 300).

The curve in FIG. 4 can be approximated by:

$$f(t) = 10^{\frac{t}{b+mt}} \tag{1}$$

where t is the sample number, f(t) is the amplitude of the sample, and b and m are parameters which may be chosen to create the best possible match between the f(t) and the data of FIG. 4.

By taking the log of both sides, equation (1) can be transformed to:

$$\log(f(t)) = \frac{t}{b+mt} \tag{2}$$

Figure 5:
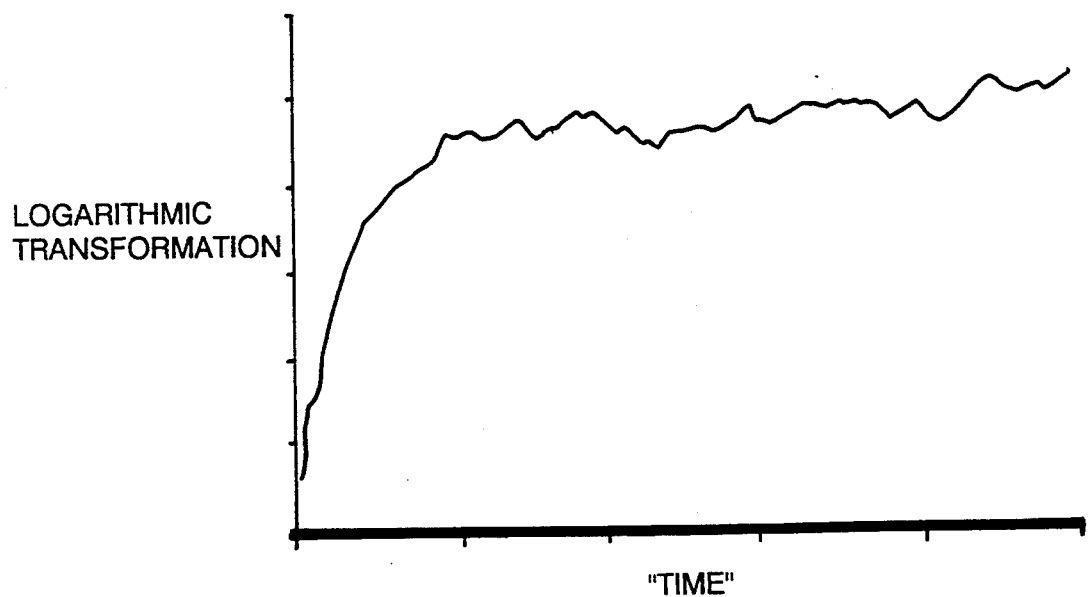
FIG. 5 is a graph of the impact energy signals of FIG. 4 after transformation via a logarithmic function.

FIG. 5 shows the curve which results from taking the log of the curve of FIG. 4; this curve approximates the right hand side of equation (2). Equation (2) can be further transformed to a linear equation by inverting both sides and multiplying by t. The result is:

$$\frac{t}{\log(f(t))} = b + mt \tag{3}$$

Figure 6:
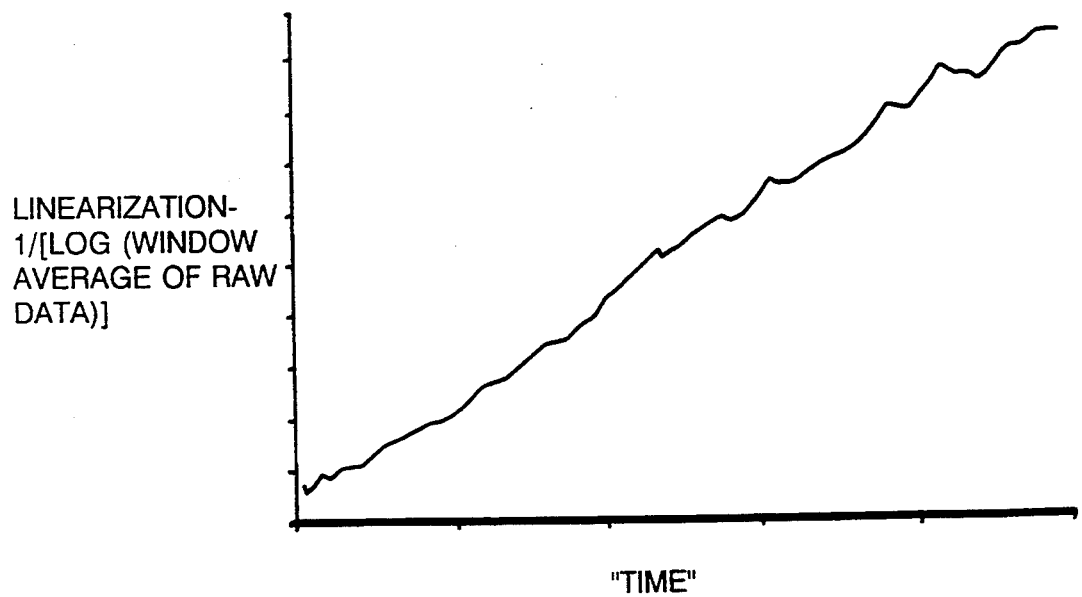
FIG. 6 is a graph of the impact energy signals of FIG. 5 after linearization.

FIG. 6 shows the curve generated by taking the inverse of the data in FIG. 5, and multiplying by t. The resulting curve is nearly a straight line (as predicted by equation (3)), demonstrating the suitability of the modelling formula in equation (1).

Equation (2) provides a useful method for determining when compaction is satisfactory. Note that the right hand side of equation (2) is a value representative of the level of compaction of the soil. As $t \to \infty$, the right hand side of equation (2) approaches the constant value $1/m$. Thus, once suitable values for b and m have been selected, to determine whether total compaction has occurred, microcontroller 85 compares the value of the right hand side of equation (2) (for the current value of t) to the theoretical maximum value $1/m$. If the current "window average" reaches a predetermined percentage of $1/m$ (e.g., K% of $1/m$, or K/m), compaction is considered to be satisfactory and controller 34 signals observer 36 to halt compaction.

To compute constants b and m, microcontroller 85 transforms each sample according to the left hand side of equation (3). The resulting samples form an approximately straight line, as shown in FIG. 6, which can be approximated by the expression $b+mt$. Using these linearized samples, values for b and m can be computed by any suitable linear regression technique.

Figure 7:
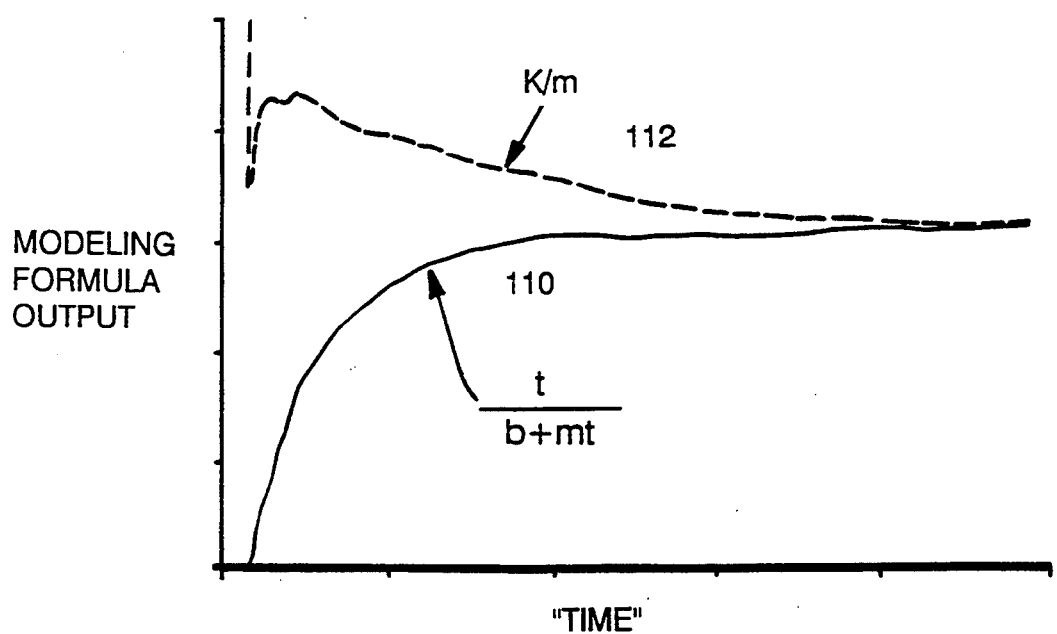
FIG. 7 is a graph showing a linearized model of the impact energy signals of FIG. 5 and demonstrating the convergence of the fitted model (data after regression) with the target maximum value K/m.

FIG. 7 illustrates the evolution of the right hand side of equation (2), which hereafter will be referred to as the "modelling formula" (curve 110) and the value K/m, which hereafter will be referred to as the "target value" (curve 112). After each sample is stored and linearized by microcontroller 85, microcontroller 85 computes new values for b and m by performing linear regression on the stored, linearized samples. As a result, the values of m and of the target value K/m are refined with every sample. After a few large initial variations (caused by the small number of samples used in the first few calculations), the values b, m, and therefore K/m, slowly converge toward constant values. At the same time, K/m converges toward the value of the modelling formula on the right hand side of equation (2) (curve 110). When the curves meet, compaction is considered to be satisfactory.

One suitable regression technique is a weighted least-squares regression, which computes the values b and m so as to minimize the value R in the equation $$R = \sum_{t=1}^{t_{MAX}} w_t(f(t) - (b+mt))^2 \tag{4}$$

where $$f(t) = \frac{t}{\log(f(t))}, \tag{5}$$

$t_{max}$ is sample number (time) of the most recent sample collected, and the $w_t$ are the weights for the regression. As is well known to those skilled in the art, the solutions to equation (4) are $$m = \frac{S_{wft} \times S_w - S_{wt} \times S_{wf}}{S_{wt2} \times S_w - (S_{wt})^2} \tag{6}$$

$$b = \frac{S_{wt2} \times S_{wf} - S_{wt} \times S_{wft}}{S_{wt2} \times S_w - (S_{wt})^2} \tag{7}$$

where $$S_w = \sum_{t=1}^{t_{MAX}} w_t, \; S_{wt} = \sum_{t=1}^{t_{MAX}} w_t t, \; S_{wf} = \sum_{t=1}^{t_{MAX}} w_t f(t) \tag{8}$$

$$S_{wft} = \sum_{t=1}^{t_{MAX}} w_t f(t) t, \text{ and } S_{wt2} = \sum_{t=1}^{t_{MAX}} w_t t^2.$$

Figure 8:
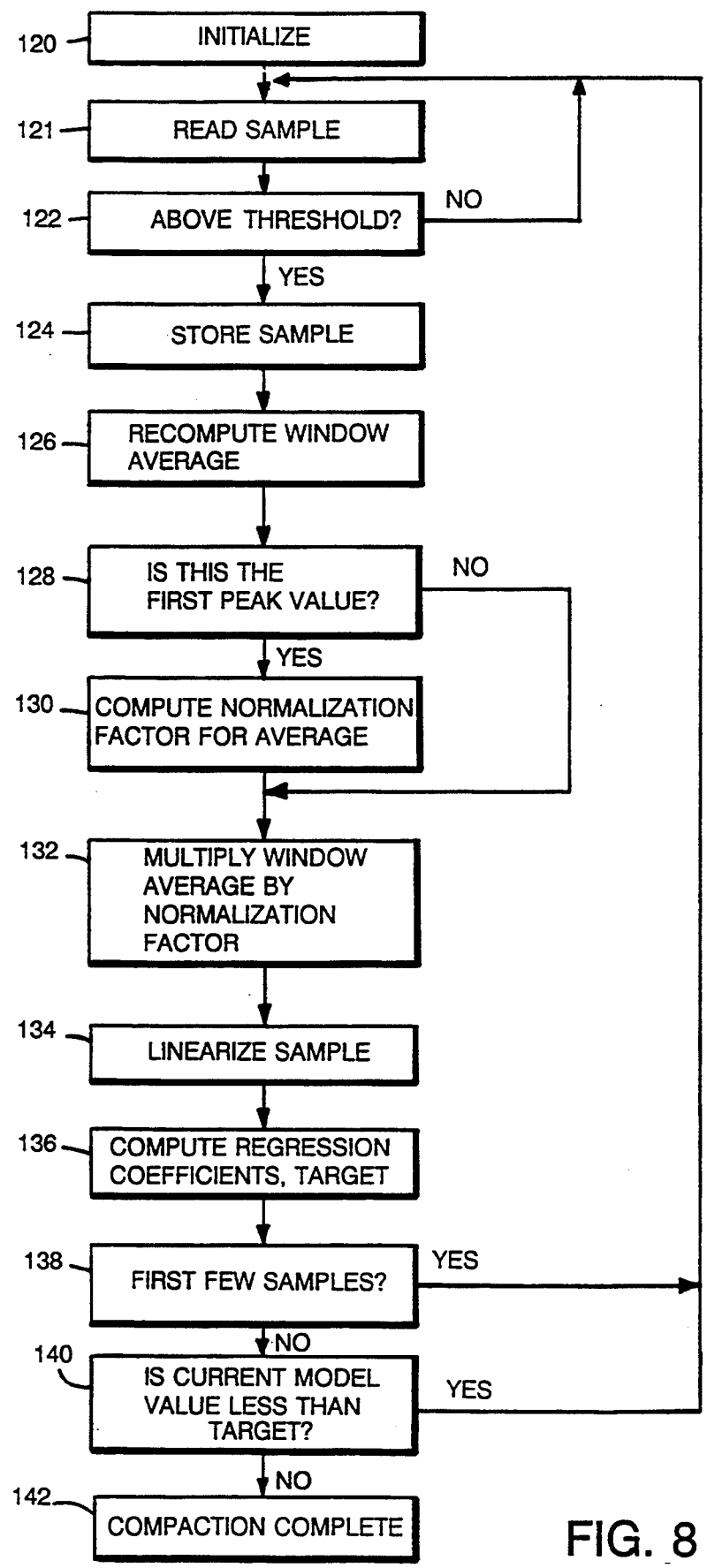
FIG. 8 is a flow chart of a process for performing smoothing and linearization of impact energy signals, and for determining complete compaction.

Appendix A shows a computer program written in the Turbo C language which performs the regression and comparison steps described above. Referring to FIG. 8, the program starts by initializing 120 all of the needed variables and arrays. Next, the program enters a loop in which it reads 121 a sample from peak detector 82 and then compares 122 the sample to the minimum threshold value. The minimum threshold should be large enough to reject the noise in peak detector 82 and analog-to-digital converter 92; since converter 92 will typically generate noise of one code the threshold should be at least two codes, and perhaps more if there is more noise in converter 92 or peak detector 82.

If the sample does not exceed the threshold, microcontroller 85 returns to step 121 and reads another sample. If, however, the sample does exceed the threshold, microcontroller 85 accepts the sample and stores it 124. Then microcontroller recomputes 126 the window-average, by adding the new sample into the current window average and subtracting the $n^{th}$ prior sample from the window average.

From one excavation to the next, the relative magnitude of the samples read from peak detector 82, and therefore the relative magnitude of the window averages, may change by an order of magnitude or more, due to variations in the distance between the source of the compacting blows and sensor 12, as well as variations in the soil type. In order to ensure that the magnitude of the computed numbers remains the same for each application, microcontroller 85 normalizes the window averages. To do this, if 128 the microcontroller has just computed the first window average, it then computes 130 a normalization factor for all of the window averages. This normalization factor is chosen so that the first window average has a small, standard value, e.g. an integer value of two. (The normalization factor in this case would be equal to two divided by the first window average value.) After computing 130 the normalization factor from the first window average, microcontroller 85 multiplies 132 the first and every subsequent window average by the normalization factor.

After normalization, microcontroller 85 linearizes 134 the current sample in the manner described by the left side of equation (3) above. Next, microcontroller 85 computes 136 new values for b and m in the manner described by equations (6), (7), (8), and then uses the new values to recompute the target value K/m.

After computing new values for b, m, and K/m, microcontroller 85 determines 138 whether the current sample is one of the first few, e.g. 3, samples. If so, the values for b and m are not stable enough to accurately model the compaction process (as illustrated by the instability of the value K/m during the first few samples in FIG. 7). If so, microcontroller 85 returns to step 121 to retrieve a new sample.

If there are sufficient samples to use the values of b and m, microcontroller 85 compares 140 the current value of the modelling formula (the right hand side of equation (2)) to the target value K/m. If the current value produced by the modelling formula is less than the target value, microcontroller 85 returns to step 121 to retrieve a new sample. Otherwise, compaction is considered to be satisfactory and microcontroller 85 signals 142 as such by displaying a suitable message on LCD display 74 and/or printing a message on printer 98, and/or generating an audible signal.

To minimize the computational effort needed to generate new values for b and m, the weights $w_t$ in equation (8) are selected so that each sample is multiplied by the same weight for each recomputation of the values b and m. Because the weights satisfy this criterion, microcontroller 85 need not completely recompute the sums of equation (8) each time a new sample is stored. Instead, microcontroller 85 can retrieve the previous values for each of these sums, and then increment each sum by the final term. Thus, $S_w$ is incremented by the value of $W_{tMAX}$, $S_{wt}$ is incremented by the value of $W_{tMAX} \cdot t_{MAX}$, and so on. One suitable formula for the weights which will satisfy this criterion is:

$$w_t = \frac{t^2}{(t + \alpha)^4} \quad (9)$$

where $\alpha$ is a constant chosen to achieve the desired relative weighting of early and recent samples (small values of $\alpha$ weight the first samples most heavily, larger values weight later samples more heavily). If t steps in integer values (i.e., the first sample is considered to be at time t=1, the second at time t=2), a suitable value for $\alpha$ is 0.5.

Other embodiments are within the following claims. For example, the material being compacted can be any progressively compactable material and need not be soil. Furthermore, the compacting energy need not be imparted by impact energy impulses. Other sources of energy pulses such as vibrators, piezoelectric transducers and explosives could also be used.

APPENDIX A
Source Code Listing

```
void peakdetect(void)
{
    double  b;          /* intercept of linearized data         */
    float   BM;         /* weighting constant, a                */
    int     boxsum;     /* sum of data points in averaging
                           window                               */
    logic   compare( ); /* function compares y* to cutoff       */
    double  data;       /* linearized data                      */
    int     getdata( ); /* function that inputs data into
                           the algorithm - getdata( )
                           idles until the next data point
                           is ready                             */
    double  logdata;    /* result of 2nd stage smoothing        */
    double  m;          /* slope of linearized data             */
    float   norm;       /* normalization constant               */
    int     peak[TMAX]; /* holds raw data, TMAX is
                           expected max # of points             */
    int     sweep;      /* time increment (in sec) be-
                           tween successive data points         */
    double  sw, swx
            swx2, swxy,
            swy;        /* regression sums                      */
    int     t;          /* time counter                         */
    int     testlevel;  /* value of current data point          */
```

-continued
APPENDIX A
Source Code Listing

```
    double  w;          /* weighting factor                     */
    int     wind;       /* averaging window size                */
    double  windave;    /* result of 1st stage smoothing        */
/** initialize counters and sums **/
    t = 0;
    norm = 1;
    boxsum = 0;
    sw = 0, swx = 0, swy = 0, swxy = 0, swx2 = 0;
/** begin the main data processing loop **/
    do      /* read data until done */
    {
        do      /* ignore data below threshold */
        {
/**input data from source **/
            testlevel = getdata( );
        } while (testlevel <= threshold);
        t += sweep;
        peak[t] = testlevel;
/*** compare( ) – checks if peak detect value has
                   reached critical point ***/
logic compare( )
{
    double cutoff;  /* compaction criteria, K/m            */
    double denom;   /* denominator for m and b             */
    double rty;     /* data after regression, y*           */
/** skip this check for the first few points **/
    if (t <= (3* sweep)) return NO;
/** complete the linear regression to calculate the slope and
    intercept for the linearized curve **/
    denom = sw * swx2 - swx * swx;
    if (denom < .0001) return NO;
    m = (sw * swxy - swy * swx) / denom;
    b = (swy * swx2 - swx * swxy) / denom;
/** reconstruct the original curve, y*, using m and b **/
    rty = t / (b + m * t);
/** the cutoff value is K/m **/
    cutoff = K/m;
/** compare **/
    if (rty > cutoff)  return YES;
    else return NO;
}
/** 1st stage smoothing **/
    boxsum += peak[t];
    if (t > wind) boxsum -= peak[t - wind];
    windave = (float)(boxsum * sweep)/(float)(wind);
    if (t == sweep) norm = 2/windave;
    windave = windave * norm;
/** 2nd stage smoothing **/
    logdata = log10(windave);
/** linearization **/
    data = t/logdata;
/** calculate regression sums **/
    w = t * t / pow((t + BM), 4);
    sw += w;
    swx += w * t;
    swy += w * data;
    swxy += w * t * data;
    swx2 += w * t * t;
/** check if compaction criteria is reached **/
    } while (!compare( ));
    printf(" *****STOP!  COMPACTION COMPLETE!*****");
```

What is claimed is:
1. A method for determining whether a compactable material is satisfactorily compacted, comprising:
delivering compaction energy pulses to said compactable material,
sensing the amount of compaction energy transmitted through said compactable material in response to energy pulses,
storing data indicative of the amount of transmitted compaction energy sensed in said sensing step,
repeating said delivering, sensing, and storing one or more times to sense and store a progression of data indicative of transmitted compaction energy, generating signals representative of a current level of compaction of said compactable material and a target level of compaction of said compactable material from said progression of data indicative of transmitted compaction energy, said generating signals step including the steps of producing a modelling formula which approximates said progression of data indicative of transmitted compaction energy, and generating a signal representative of said current level and said target level from said produced modelling formula, comparing said current level of compaction to said target level of compaction, and if said current level equals or exceeds said target level, determining that said compactable material is satisfactorily compacted.

2. The method of claim 1 wherein said compactable material is soil.

3. The method of claim 1 further comprising after determining that said compactable material is satisfactorily compacted, signalling satisfactory compaction to an operator.

4. The method of claim 1 wherein said modelling formula approaches a fixed asymptotic value, and said target level of compaction is a fraction of said asymptotic value.

5. The method of claim 4 wherein said modelling formula is $$10^{\frac{t}{b+mt}}$$

where t is the number of the repetition of said sensing step during which transmitted compaction energy is sensed, and b and m are parameters which are adjusted to approximate said formula to said progression of data.

6. The method of claim 1 wherein sensing the amount of compaction energy comprises repeatedly sensing the peak amplitude of an electrical signal generated by a sensor over successive sampling periods, and retaining only those peak amplitudes larger than a predetermined threshold.

7. The method of claim 4 wherein sensing the amount of compaction energy comprises repeatedly sensing the peak amplitude of an electrical signal generated by a sensor over successive sampling periods, and retaining only those peak amplitudes larger than a predetermined threshold.

8. The method of claim 7 wherein sensing the amount of compaction energy further comprises forming a low-pass filtered version of said retained peak amplitudes.

9. The method of claim 8 wherein forming a low-pass filtered version of a peak amplitude comprises averaging said peak amplitude with other peak amplitudes sensed during prior repetitions of said sensing step.

10. The method of claim 8 wherein sensing the amount of compaction energy further comprises forming a logarithmic transformation of said low-pass filtered version of said retained peak amplitudes.

11. The method of claim 10 wherein sensing the amount of compaction energy further comprises applying a linear regression to said logarithmic transformation of said low-pass filtered version of said retained peak amplitudes.

12. The method of claim 11 wherein applying said linear regression includes applying a weighting formula to said logarithmic transformation of said low-pass filtered version of said retained peak amplitudes.

13. The method of claim 12 wherein said compactable material is soil.

14. The method of claim 13 further comprising after determining that said compactable material is satisfactorily compacted, signalling satisfactory compaction to an operator.

* * * * *